(12) United States Patent
Greenwald et al.

(10) Patent No.: US 7,231,245 B2
(45) Date of Patent: Jun. 12, 2007

(54) SYSTEM AND METHOD OF ASSESSMENT OF NEUROLOGICAL CONDITIONS USING EEG

(75) Inventors: Scott D. Greenwald, Norfolk, MA (US); Charles P. Smith, Medway, MA (US); Jeffrey C. Sigl, Medway, MA (US); Philip H. Devlin, Brookline, MA (US)

(73) Assignee: Aspect Medical Systems, Inc., Norwood, MA (US)

( * ) Notice: Subject to any disclaimer, the term of this patent is extended or adjusted under 35 U.S.C. 154(b) by 0 days.

(21) Appl. No.: 10/337,088

(22) Filed: Jan. 6, 2003

(65) Prior Publication Data

US 2003/0181821 A1 Sep. 25, 2003

Related U.S. Application Data

(60) Provisional application No. 60/345,433, filed on Jan. 4, 2002.

(51) Int. Cl.
    A61B 5/04 (2006.01)
(52) U.S. Cl. .................................................. 600/544
(58) Field of Classification Search ............... 600/544, 600/545
    See application file for complete search history.

(56) References Cited

U.S. PATENT DOCUMENTS

| | | | |
|---|---|---|---|
| 4,533,346 A * | 8/1985 | Cosgrove et al. ............. 604/66 |
| 4,907,597 A | 3/1990 | Chamoun | |
| 5,010,891 A | 4/1991 | Chamoun | |
| 5,230,346 A | 7/1993 | Leuchter et al. ............. 128/731 |
| 5,269,315 A | 12/1993 | Leuchter et al. | |
| 5,309,923 A | 5/1994 | Leuchter et al. ............. 128/731 |
| 5,311,876 A | 5/1994 | Olsen | |
| 5,320,109 A * | 6/1994 | Chamoun et al. ........... 600/544 |
| 5,458,117 A | 10/1995 | Chamoun et al. | |
| 5,846,208 A | 12/1998 | Pichlmayr | |
| 6,024,707 A | 2/2000 | Scinto et al. ................ 600/558 |
| 6,343,229 B1 | 1/2002 | Siebler | |
| 6,622,036 B1 * | 9/2003 | Suffin ......................... 600/544 |

OTHER PUBLICATIONS

Alkire, Michael T., "Quantitative EEG Correlations with Brain Glucose Metabolic Rate during Anesthesia In Volunteers," Anesthesiology 1998, vol. 89, pp. 323-333.

Besthorn, C., et al., "Discrimination of Alzheimer's Disease and Normal Aging by EEG Data," Electroencephalography and Clinical Neurophysiology 1997, vol. 103, pp. 241-248.

(Continued)

Primary Examiner—Max Hindenburg
Assistant Examiner—Navin Natnithithadha
(74) Attorney, Agent, or Firm—Wilmer Cutler Pickering Hale and Dorr LLP

(57) ABSTRACT

The present invention is a system and method that produces features and indices that indicate the presence or absence of a disease or condition, or of the progression of a disease or condition. The system and method of the present invention also produce features and indices that predict responsiveness to medication from a premedication baseline. The system and method of the present invention further incorporates a testing methodology to improve the performance characteristics of the features or indices. To obtain such features and indices, time domain, power spectrum, bispectrum and higher order spectrum values are derived from biopotential signals taken from the subject being tested.

21 Claims, 6 Drawing Sheets

OTHER PUBLICATIONS

Claus, J.J., et al., "The Diagnostic Value of Electroencephalography in Mild Senile Alzheimer's Disease," Clinical Neurophysiology 1999, vol. 110, pp. 825-832.

Coben, L.A., et al, "A Longitudinal EEG Study of Mild Senile Dementia of Alzheimer Type: Changes at 1 Year and at 2.5 Years," Electroencephalogr. Clin. Neurophysiol. 1985, vol. 2, pp. 101-112.

Cook, Ian A., et al, "Prefrontal Changes and Treatment Response Prediction in Depression," Seminars in Clinical Neuropsychiatry, 2001, vol. 6, pp. 113-120.

Diego, Niguel, A., et al., "CES-D Depression Scores are Correlated with Frontal EEG Alpha Asymmetry," Depression and Anxiety 2001, vol. 13, pp. 32-37.

Folstein, Marshall F., et al "Mini-Mental State" "A Practical Method for Grading the Cognitive State of Patients for the Clinican," J. Psychiat res. 1975, vol. 12, pp. 189-198.

Glass, Peter S., et al., "Bispectral Analysis Measures Sedation and Memory Effects of Propofol, Midazolam, Isoflurane, and Alfentanil in Health Volunteers," Anesthesiology, 1997, vol. 86, pp. 836-847.

Hamilton, Max, "A Rating Scale for Depression," J. Neurol. Neurosurg. Psychiat., 1960, vol. 23, pp. 56-62.

Hassainia, F., et al. "Quantitative EEG and Statistical Mapping of Wakefulness and REM Sleep in the Evaluation of Mild to Moderate Alzheimer's Disease," Eur. Neurol. 1997, vol. 37, pp. 219-224.

Holschneider, Daniel P., et al., "Loss of High-Frequency Brain Electrical Response to Thipental Administration in Alzheimer's-Type Dementia," Neurophychopharmacology 1997, vol. 16, pp. 26-275.

Jonkman, E.J., "The Role of the Electroencephalogram in the Diagnosis of Dementia of the Alzheimer Type: an Attempt at Technology Assessment," Neurophysiol. Clin. 1997, vol. 27, pp. 211-219.

Knott, Verner J., "Quantitive EEG in the Prediction of Antidepressant Response to Imipramine," J. Affective Disorders, 1996, vol. 39, pp. 175-184.

Knott, V., et al., "Pre-Treatment EEG at It's Relationship to Depression Severity and Paroxetine Treatment Outcome," Pharmacopsychiatry 2000, vol. 33, pp. 201-205.

Leuchter, Andrew F., "Regional Differences in Brain Electrical Activity in Dementia: Use of Spectral Power and Spectral Ratio Measures," Electroencephalography and Clinical Neurophysiology, 1993, vol. 87, pp. 385-393.

McKhann, Guy, et al., "Clinical Diagnosis of Alzheimer's Disease: Report of the NINCDS-ADRDA Work Group Under the Auspices of Department of Health and Human Services Task Force on Alzheimer's Disease," Neurology, 1984, vol. 34, pp. 939-944.

Neufeld, M.Y., "Effects of a Single Intravenous Dose of Scopolamine on the Quantitative EEG in Alzheimer's Disease Patents and Age-Matched Controls," Electroencephalography and Clin. Neurophysiology, 1994, vol. 91, pp. 407-412.

Pezard, Laurent, "Entropy Maps Characterizer Drug Effects on Brain Dynamics in Alzheimer's Disease," Neuroscience Letters, 1998, vol. 253, pp. 5-8.

Rampil, Ira J., A Primer for EEG Signal Processing in Anesthesia, Anesthesiology, 1998, vol. 89, pp. 980-1002.

Renna, Maurizio, "Does Dementia Affect the Bispectal Index?" Amer. Society of Anesthesiologists, 2001, p. 1 of 2.

Struys, M.D., Michel, RUGLOOP Software, University of Gent, Department of Anaesthesia, Belgium.

* cited by examiner

SYSTEM AND METHOD OF ASSESSMENT OF NEUROLOGICAL CONDITIONS USING EEG

BACKGROUND OF THE INVENTION

This invention relates to assessing neurological conditions and more particularly to the diagnosis and monitoring of progression of dementia, the assessment of depression and the prediction of depression treatment efficacy. The invention may also be applied to diagnosing and monitoring epilepsy, Parkinson's disease, attention deficit (hyperactive) disorder, stroke, delirium, vigilance and sleep assessment.

Dementia is a generalized designation for a state of mental deterioration, manifested in cognitive dysfunction, such as memory loss, impaired thinking, and strange behavior. There are many types and causes of dementia, including vascular dementia, Alzheimer's type dementia (ATD), HIV/AIDS-related dementia, alcoholic dementia, depression, Huntington's disease, tumors and Parkinson's disease. ATD is the most common type of dementia and is a progressive, neurological disorder of the brain. ATD is the fourth leading cause of death in adults, after heart disease, cancer, and stroke.

Early diagnosis of ATD is desirable for several reasons. If the dementia is due to a cause other than Alzheimer's disease, it is often treatable. Identification of a cause other than Alzheimer's disease also relieves concern about the prognosis. Finally, a diagnosis of ATD at an early stage allows the afflicted and their family an opportunity for medical and financial planning. In addition, while the current treatment methods for ATD offer only short-term symptomatic relief, there are numerous treatments and prevention methods in development that promise a radically improved level of treatment. The widespread application of such therapies will require a much more effective method of diagnosing ATD in its earliest stages, before other symptoms have made their appearance. Even at present, early diagnosis is important to identify other symptomatically similar disease processes that are often easily treated and possibly reversed.

There is no definitive test for ATD; only by studying brain sections obtained during an autopsy may one conclusively arrive at a diagnosis of "definite ATD". The most definitive diagnosis that may be obtained during the course of the illness is that of "probable Alzheimer's type dementia". This diagnosis is typically arrived at by a rule-out procedure. Other disease processes that could produce similar symptoms are systematically ruled out using a standardized decision tree, generally the NINCDS-ADRDA criteria. This diagnosis of "probable ATD" is not always correct, however. When histopathological findings are compared with the clinical diagnosis following autopsy, it appears that 80–88% of clinical diagnoses are correct. The application of the NINCDS-ADRDA criteria is time-consuming and requires a degree of expertise that is not available to all general practitioners, internists and psychologists. Moreover, these methods are only applicable after the onset of symptoms such as memory loss and confusion.

Patients with dementia of many types (ATD, vascular, etc.) exhibit changes in EEG in comparison to age-matched normal subjects. Typical changes include increased EEG activity in the delta (0–4 Hz) and theta (4–8 Hz) bands and decreased EEG activity in the beta band (12–30 Hz). This is in contrast to elderly normal subjects, who exhibit decreased low frequency activity and increased high frequency activity with increasing age. In addition to differences between normal patients and those with dementia, there are characteristic changes in the EEG power spectra observed at progressively worsening levels of cerebral function, implying a progressive change in EEG parameters that may be used to stage the progression of the dementia. The change in theta power as a percent of the total power has been shown to distinguish between mild, moderate and severe dementia, as well as controls.

The EEG observed in patients with ATD exhibits specific characteristics that are different from those observed in cognitively normal, aged patients. Numerous published studies have reported on the analysis of electroencephalographic signals (EEG) with the objective of identifying patients with ATD. These studies and methods are generally designed to differentiate ATD patients from normal subjects and/or patients having dementias with similar symptoms but different etiologies, such as vascular infarcts. These methods generally utilize discriminant analyses or neural networks based upon various processed EEG parameters designed to quantify the changes in EEG typically observed in ATD (e.g., alpha power, the power observed in the 8–14 Hz band of the EEG power spectrum). The median accuracy of a variety of methods for differentiating ATD patients from cognitively normal controls in a series of 16 EEG studies was 81%, with a range of 54–100%. In general, these methods have reported sensitivities and specificities in the 80% range, approximately equivalent to that achievable by an expert clinician deriving a diagnosis from a clinical interview and history. However, it must be noted that in almost all studies the criteria used to differentiate normals from ATD were defined using the data in the analysis. There are few prospective studies that used a first population to develop a criterion and then applied that criterion to a second population. Thus, the actual accuracy of existing methods is difficult to determine.

Several investigators have proposed the use of a drug challenge for the assessment of dementia. Holschneider reported differential changes in the power in the 20–28 Hz spectral band in normal, ATD and vascular dementia subjects following administration of a thiopental bolus. While both normal and vascular dementia subjects showed significant increases in 20–28 Hz log power compared to baseline, the ATD subjects exhibited no change from baseline. Neufeld used a similar protocol to determine the differential effect of a dose of scopolamine between age-matched normal subjects and those with ATD. At baseline, ATD patients exhibited smaller absolute and relative alpha amplitudes (8–11.5 Hz) and larger relative theta amplitudes (4–7.5 Hz) compared with normal subjects. After intravenous administration of 0.5 mg scopolamine, the normal subjects exhibited a larger increase in absolute and relative delta amplitude (1–3.5 Hz) than the ATD subjects in comparison to a placebo. Scinto demonstrated a method of diagnosing Alzheimer's disease using an automated apparatus that can continuously monitor pupil diameter before and after the administration of a neural transmitter mediator to the targeted eye. The presence of hypersensitivity to the administered neural transmitter mediator serves as a marker of Alzheimer's disease.

Depression is a mood disorder that affects 17 million Americans each year, and is responsible for 9.7 million doctor visits. It affects sufferers in a variety of ways, resulting in depressed mood, irritability, sleep disorders, feelings of agitation; guilt and worthlessness, loss of energy and initiative, an inability to concentrate and an increased incidence of suicide. It is difficult to diagnose, due to comorbidities and the fact that it is largely self-reported.

There are a number of antidepressant pharmacological agents, and once the proper treatment is determined, their effectiveness is quite high. Selection of the most efficacious agent and the initial dose is largely by trial and error. There is thus a need for an objective measure of depression as well as a method of predicting efficacy of antidepressant treatment. Diego, et al. found that the level of depression was correlated with frontal EEG alpha asymmetry and left frontal EEG alpha power. In another study, EEG theta activity was correlated with pre-treatment level of depression, and improved level of depression with treatment was correlated with slow (delta and theta) activity and fast (beta) activity at frontal recording sites. Still others have demonstrated that prefrontal EEG response to antidepressant medication therapy was seen as early as 48 hours after initiation of treatment and such changes preceded clinical response. These changes were absent in non-responders. Another earlier study reported small but statistically significant differences in pre-treatment theta power between responders and non-responders to an antidepressant medication. None of these methods have resulted in a device with high enough sensitivity and specificity to be clinically useful.

A commercially available device that uses bispectral analysis of the EEG is the Bispectral Index™ (BIS™). BIS is a univariate processed EEG parameter derived from surface electrodes placed on the forehead and temple. The Bispectral Index is described in U.S. Pat. Nos. 4,907,597; 5,010,891; 5,320,109 and 5,458,117, all of which are incorporated herein by reference. BIS is a complex parameter, consisting of a set of components that include power spectral and higher order (bispectral) components as well as time domain components. These components are combined into a single number scaled from 0 to 100. BIS has been designed to reflect the hypnotic state of an individual, both while awake and while undergoing anesthesia. In a patient under the influence of anesthetic agents, the probability of recall is closely related to the hypnotic state. For this reason, BIS is highly correlated with the probability of both free and cued recall in subjects under the influence of anesthetic and sedative agents. Decreased formation of new memories and an impaired ability to recall preexisting memories are hallmarks of various dementias. In certain progressive dementias, such as ATD, the degree of memory impairment increases as the disease progresses. BIS was observed to be lower at unmedicated, presurgical baseline in patients with dementia (ATD and multi-infarct dementia) compared to age-matched control subjects. It is well known that cerebral glucose metabolism is decreased in patients with ATD in comparison to age-matched patients with normal cognitive function. BIS was shown to be correlated with reduction of cerebral glucose metabolism resulting from anesthetic agents, as determined using positron emission tomography imaging. It is thus a reasonable conjecture that the one of the underlying technologies of BIS, bispectral analysis, might be useful in assessing neurological function in a global sense.

SUMMARY OF THE INVENTION

The present invention is a system and method that produces features and indices that indicate the presence or absence of a disease or condition, or of the progression of a disease or condition. The system and method of the present invention also produce features and indices that predict responsiveness to medication from a premedication baseline. The system and method of the present invention further incorporates a testing methodology to improve the performance characteristics of the features or indices. To obtain such features and indices, power spectrum, time domain, bispectrum and higher order spectrum values are derived from biopotential signals taken from the subject being tested.

DETAILED DESCRIPTION OF THE PREFERRED EMBODIMENTS

Figure 1:
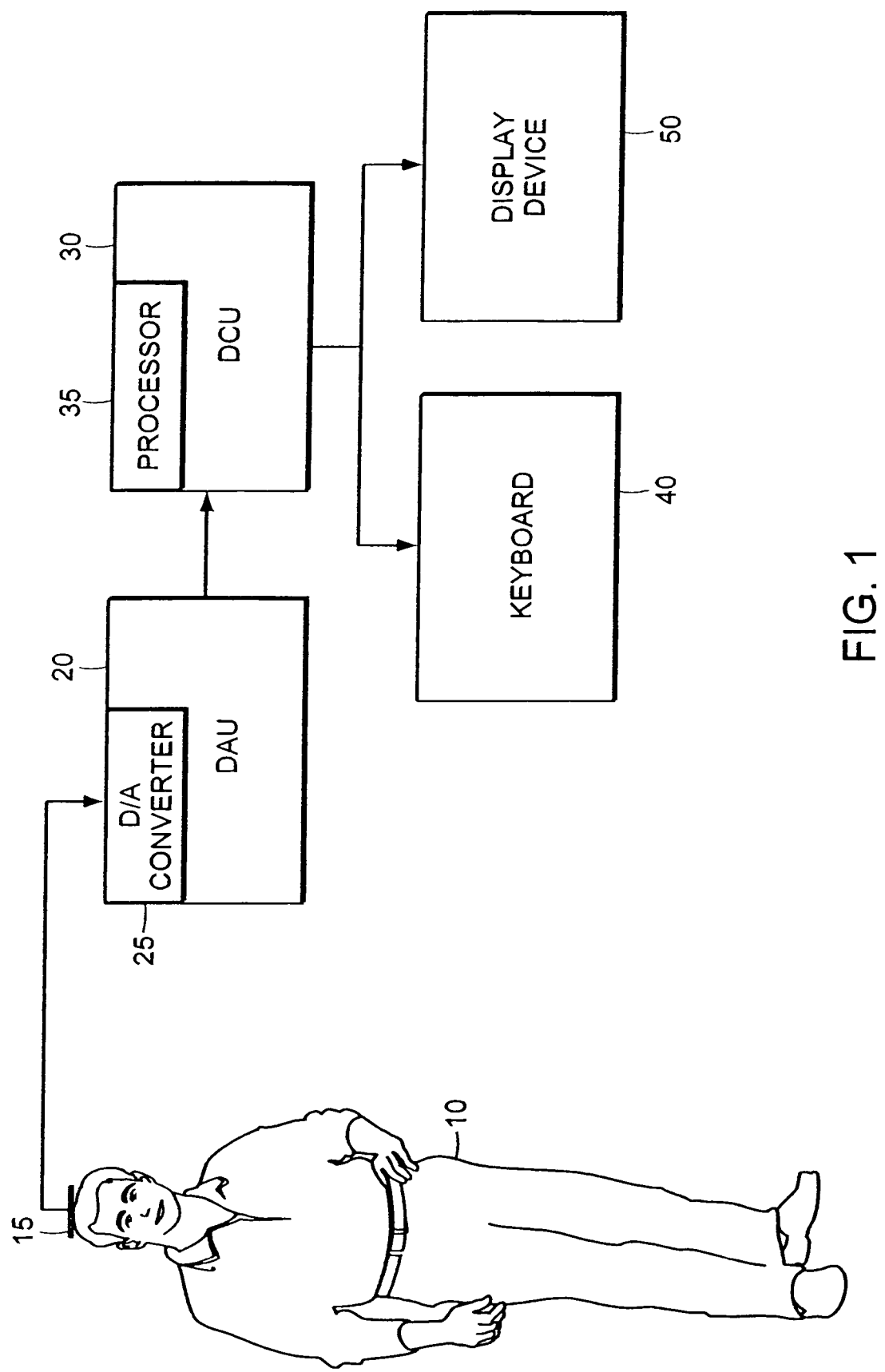
FIG. 1 is a block diagram of the system of the present invention.

A preferred embodiment of the present invention shown in FIG. 1 incorporates a Data Acquisition Unit (DAU) 20 that is used to acquire an EEG signal from a subject 10 for subsequent processing. The DAU 20 typically consists of a computer system with an integral analog-to-digital (A-D) converter 25 and a set of electrodes that is representatively shown placed on the scalp of a subject 10. While only a single electrode 15 is shown, any montage of electrodes used to obtain EEG signals may be used in the invention. The A-D converter 25 is used to transform the analog EEG signals obtained from the electrodes 15 into a sampled set of signal values that may then be analyzed by the processor 35 of a Data Computation Unit (DCU) 30. The DCU 30 incorporates a processor 35 and a communications device that receives the sampled values from the DAU 20. In the described embodiment, the processors of the DAU 20 and DCU 30 are one and the same. In an alternate embodiment, however, the DAU 20 may acquire the EEG signals and transmit the sampled EEG signals over a communications link to a remote DCU 30. Such a communications link may be a serial or parallel data line, a local or wide area network, a telephone line, the Internet, or a wireless connection. The clinician conducting the assessment may communicate with the DCU 30 using a keyboard 40 and display device 50. In the alternate embodiment that utilizes a DCU 30 remote from the DAU 20, an additional keyboard and display device may be attached to the DAU 20 for the use of the clinician.

After the DCU 30 receives the sampled values from the DAU 20, the DCU 30 first examines the sampled EEG signals for artifact arising from patient movement, eye blinks, electrical noise, etc. Detected artifact is either removed from the signal, or the portion of the signal with artifact is excluded from further processing. The EEG signal is also filtered to reduce or remove artifact from high and/or low frequency noise sources, such as electromyographic and radio frequency interference and movement artifact, respectively. High-pass filtering is also employed to reduce the tendency of power at frequencies above the signal band of interest from appearing at lower frequencies due to an inadequate sampling frequency (aliasing). The DCU 30 next computes the set of bispectral arrays from the artifact-free EEG data, as well as additional non-bispectral parameters. Non bispectral parameters may include power spectral arrays, higher-order spectral arrays (trispectrum, etc.), cordance (such as described in U.S. Pat. No. 5,269,315 and U.S. Pat. No. 5,309,923), z-transformed variables, entropy parameters, and time-domain parameters, including but not limited to template matching, peak detection, threshold crossing, zero crossings and Hjorth descriptors. Such parameters, bispectral or otherwise, which quantify some aspect of the data are referred to as features. An index is a function incorporating one or more features as variables. The index function may be linear or nonlinear, or may have an alternative form such as a neural network. The DCU 30 calculates from all the bispectral arrays and non-bispectral parameters a series of features and indices that are indicative of the subject's level of neurological dysfunction, the severity of a neurological condition, or the likelihood of responsiveness to pharmacological treatment. These features and indices may be displayed to the user on the display device 50. In the embodiment in which the DCU 30 is remote from the DAU 20, the result may be transmitted back to the display device on the DAU 20, or transmitted to the patient's physician via e-mail or made available via a secure internet World Wide Web page.

When the electrodes are all to be placed below the hairline, the electrodes are preferably of the Zipprep® type manufactured by Aspect Medical Systems, Inc. (Newton, Mass.). When electrodes are placed within the hair, gold-cup type electrodes may be used, held in place by either collodion or a physical restraint such as an electrode cap placement device, as provided by various manufacturers. A variety of different electrode placements, or montages, may be used.

Calculation of the Bispectral Arrays

The bispectral arrays may be calculated using frequency domain (Fourier transform) methods as well as time domain (autoregressive) methods. The term bispectral arrays or bispectrum includes all or any of the following arrays, for both auto and cross formulations: complex triple product, real triple product, bispectral density, biphase and bicoherence arrays. In addition, the power spectral arrays are calculated as an intermediate step and are available for the derivation of parameters to be used as features in an index. Both methods will be illustrated here, and those skilled in the art will recognize that other methods may potentially be derived, as well. The invention is intended to incorporate all computational methods.

Figure 2:
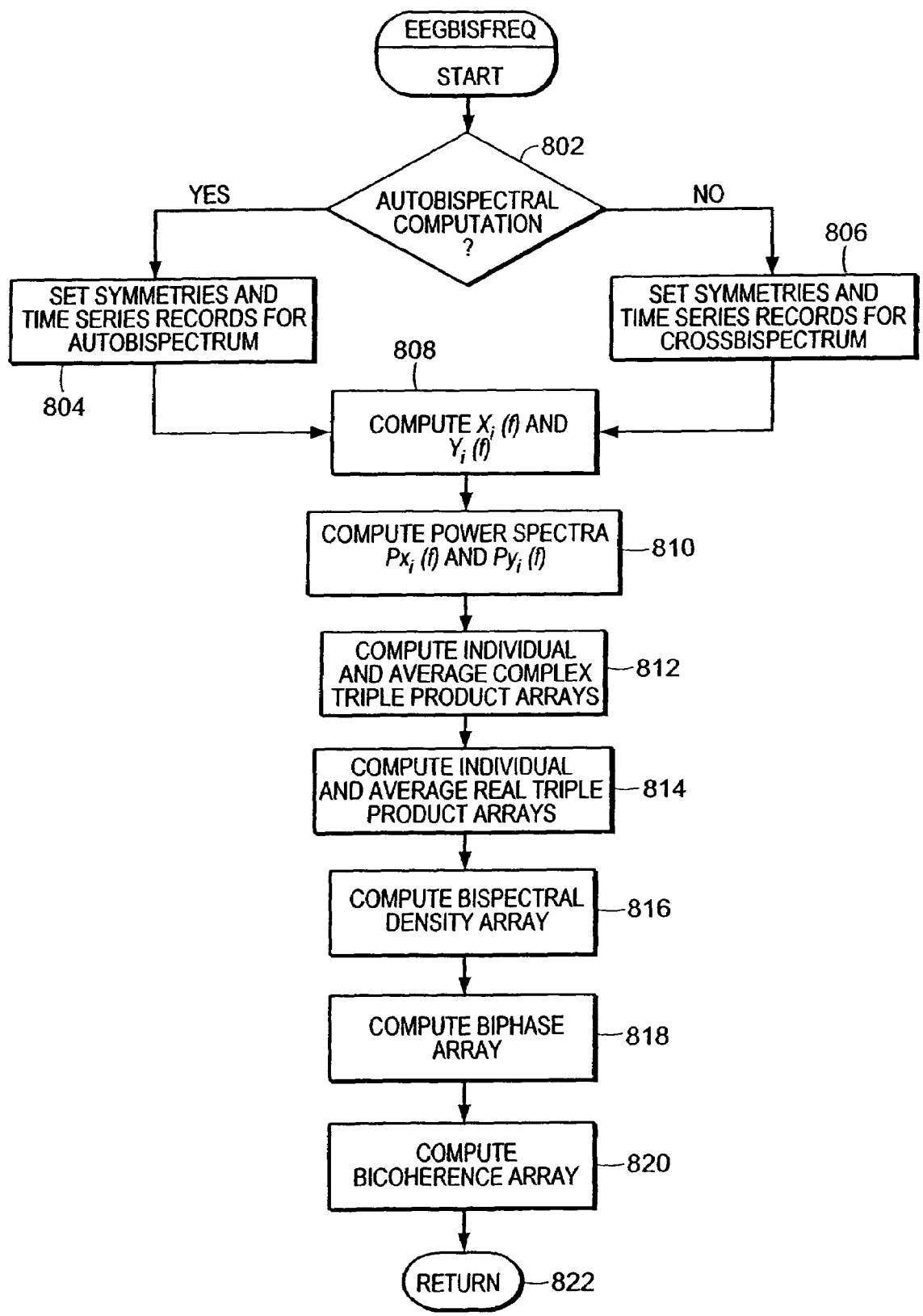
FIG. 2 is a flow chart of a method of computation of the auto/cross bispectral arrays of the present invention.

Referring now to FIG. 2, the frequency domain based procedures for producing the autobispectral or the cross-bispectral arrays will now be described. In step 802, the system checks whether the computation to be performed is an autobispectral or cross-bispectral computation. Autobispectral analysis is a special case of cross-bispectral analysis and therefore different rules of symmetry apply.

In step 804, the system sets the following symmetries in order to proceed with autobispectral computation:

$$f_1+f_2 \leq f_s/2$$

$$0 \leq f_2 \leq f_1$$

where $f_s$ is the sampling rate (128 samples/second in the preferred embodiment which uses 128 2-second records, resulting in a frequency resolution of 0.5 Hz), and $f_1$ and $f_2$ (also referred to as Frequency 1 and Frequency 2) denote the frequency pairs over which bispectral computation will be carried out. In addition, for the autobispectral computation, $$X_i(t)=Y_i(t) \rightarrow X_i(f)=Y_i(f)$$

$X_i(t)$ and $Y_i(t)$ denote the individual time series records used for bispectral computation. $X_i(f)$ and $Y_i(f)$ denote the Fourier transforms of the time series records $X_i(t)$ and $Y_i(t)$, respectively, and i denotes the record number.

In step 806, the following symmetries are adhered to for cross-bispectral analysis:

$$f_1+f_2 \leq f_s/2$$

$$0 \leq f_1 \leq f_s/2$$

$$0 \leq f_2 \leq f_s/2$$

$$X_i(t) \neq Y_i(t) \rightarrow X_i(f) \neq Y_i(f)$$

where all variables represent the same values as they do for autobispectral analysis, except that for cross-bispectral analysis $X_i(t)$ and $Y_i(t)$ represent individually derived time series records.

The fast Fourier transform (FFT) $X_i(f)$ and $Y_i(f)$ of the selected records is computed using a standard IEEE library software routine or any other publicly available software routine in step 808.

In Step 810, the power spectra $P_{Xi}(f)$ and $P_{Yi}(f)$ of each of the selected records is computed by squaring the magnitudes of each element of the Fourier transforms $X_i(f)$ and $Y_i(f)$, respectively.

The system computes the average complex triple product in step 812 by utilizing the following equations where $bc_i(f_1,f_2)$ is the individual complex triple product from one record and $BC(f_1,f_2)$ is the average complex triple product:

$$bc_i(f_1,f_2)=X_i(f_1)Y_i(f_2)Y_i^*(f_1+f_2)$$

where $Y_i^*(f_1+f_2)$ is the complex conjugate of $Y_i(f_1+f_2)$, and $$BC(f_1, f_2) = \frac{1}{M}\sum_{i=1}^{M} bc_i(f_1, f_2)$$

where M is the number of records (128 in the preferred embodiment).

The average real triple product is computed in step 814 by using the following equations where $P_{Xi}(f)$ and $P_{Yi}(f)$ are the power spectra from one record, $br_i(f_1,f_2)$ is an individual real triple product from one record and $BR(f_1,f_2)$ is the average real triple product:

$$br_i(f_1,f_2)=P_{Xi}(f_1)P_{Yi}(f_2)P_{Yi}(f_1+f_2)$$

$$BR(f_1, f_2) = \frac{1}{M}\sum_{i=1}^{M} br_i(f_1, f_2)$$

Note that $P_{Yi}$ is real valued, and therefore $P_{Yi}=P_{Yi}^*$.

In step 816, the bispectral density array $BD(f_1,f_2)$ is computed as the magnitude of $BC(f_1,f_2)$ using the following equation:

$$BD(f_1,f_2)=|BC(f_1,f_2)|$$

In step 818, the system computes the biphase array $\phi(f_1,f_2)$ using the following equation:

$$\phi(f_1, f_2) = \tan^{-1}\left(\frac{\text{Im}(BC(f_1,f_2))}{\text{Re}(BC(f_1,f_2))}\right)$$

$$0 \leq \phi \leq 2\pi (\text{radians})$$

In step 820, the system computes the bicoherence array $R(f_1,f_2)$ using the following equation:

$$R(f_1, f_2) = \frac{BD(f_1, f_2)}{\sqrt{BR(f_1, f_2)}}$$

$$0 \leq R \leq 1$$

In step 822, the system returns the requested auto/cross bispectral arrays to the Data Computation Unit 30.

Figure 3:
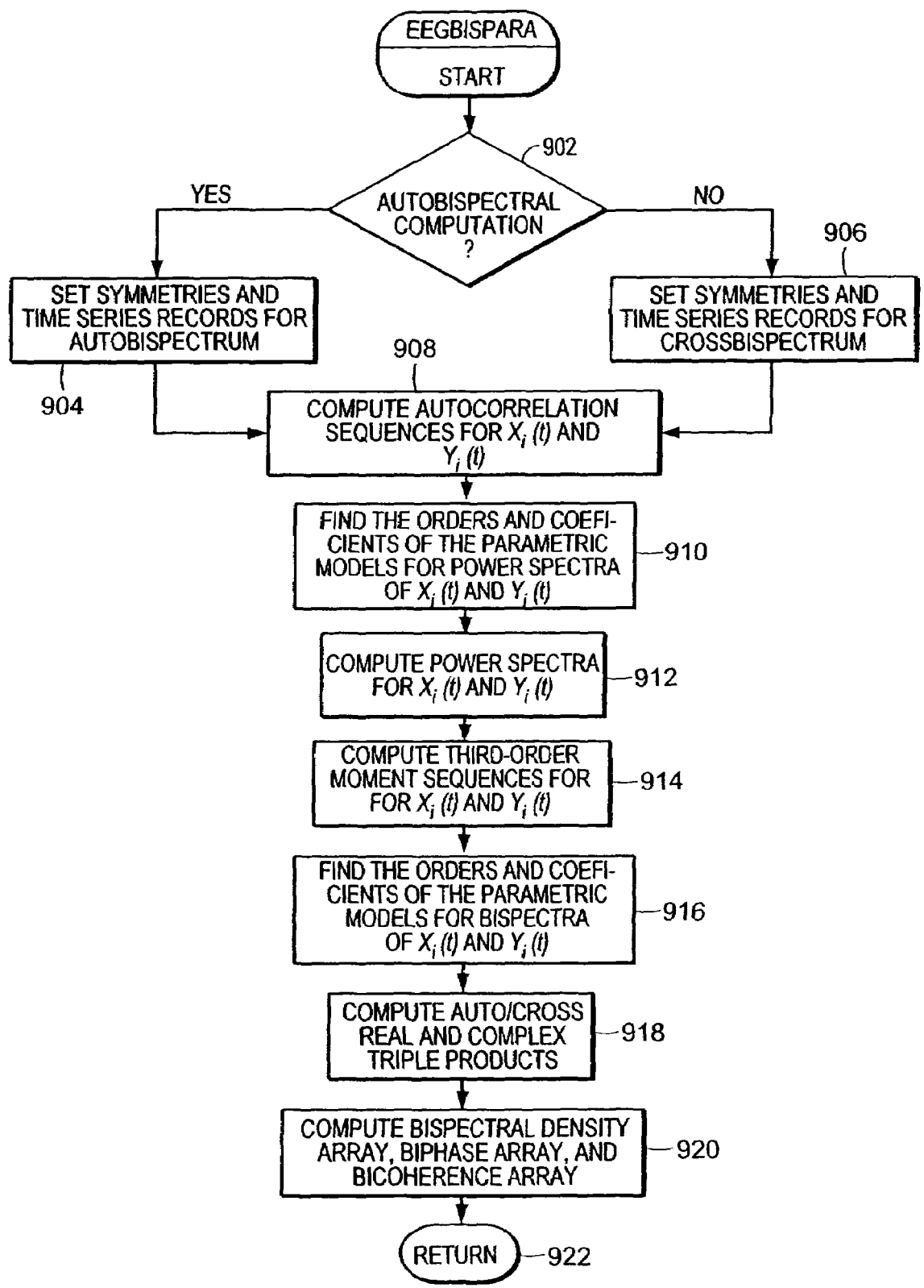
FIG. 3 is flow chart of an alternate method of computation of the auto/cross bispectral arrays of the present invention.

Turning now to FIG. 3, a parametric based method for calculating the auto/cross bispectral arrays will now be described. In steps 902, 904, and 906 the system sets the symmetries and time series records in the same manner as described above in steps 802, 804, and 806 respectively. The power spectra of $X_i(t)$ and $Y_i(t)$ are estimated in steps 908, 910, and 912. This estimation method includes two major stages, the autoregressive (AR) model order selection and the power spectrum computation for $X_i(t)$ and $Y_i(t)$. In step 908, the system computes two sequences of autocorrelations, $\{R_{2X}(m)\}$ and $\{R_{2Y}(m)\}$ using the following equation.

$$R_{2z}(m) = \frac{1}{M*N} \sum_{i=1}^{M} \sum_{t=0}^{N-|m|} z_i(t)z_i(t+m)$$

$z=X,Y$, and $m=0, 1, \ldots, L$ where M is the number of records and N is the number of samples per record (128 and 256, respectively, in the preferred embodiment), and L is much greater than the possible AR filter order (L=50 in the preferred embodiment). The Final Prediction Errors, $FPE_X(m)$ and $FPE_Y(m)$ are calculated for all orders, m=0, 1, 2, . . . L, by performing a Levinson recursion function on each autocorrelation sequence in step 910 in order to find the order of the AR filter. The locations of the minima of $FPE_X(m)$ and $FPE_Y(m)$, $Q_X$ and $Q_Y$, respectively, are chosen to be the orders of the AR filters of power spectra of $X_i(t)$ and $Y_i(t)$ respectively, i.e., $FPE_X(Q_X)=\min\{FPE_X(m)\}$ $FPE_Y(Q_Y)=\min\{FPE_Y(m)\}$ Once the orders of the AR filters for power spectra are chosen, the autocorrelation sequences, $\{R_{2X}(m)\}$ and $\{R_{2Y}(m)\}$, are entered into Levinson recursion with orders $Q_X$ and $Q_Y$, respectively, instead of L. The coefficients, $\{c_{iX}, i=0, 1, \ldots, Q_X\}$ and $\{c_{iY}, i=0, 1, \ldots, Q_Y\}$, obtained from the recursion are the coefficients of the AR filters for the power spectra of $X_i(t)$ and $Y_i(t)$, respectively. Then, in step 912, the power spectra $P_X(f)$ and $P_Y(f)$ are computed as the prediction error ($\sigma_z^2$) divided by square of the magnitude of the Fourier transform of the coefficients, i.e., $$P_z(f) = \frac{\sigma_z^2}{\left|1 + \sum_{i=1}^{Q_z} c_{iz}e^{-j2\pi fi}\right|^2}$$

$z = X, Y$

The system estimates the auto/cross real and complex triple products in steps 914, 916, and 918. The estimation process includes two major stages: the order selection and real and complex triple product computation. In step 914, two sequences of third-order moments, $\{R_{3X}(\tau)\}$ and $\{R_{3Y}(\tau)\}$ are computed using the following equation.

$$R_{3z}(\tau) = \frac{1}{M*N} \sum_{i=1}^{M} \sum_{t=s_1}^{s_2} z_i(t)z_i^2(t+\tau)$$

$z = X, Y$, and $\tau = -L, \ldots, L$ where $s_1=\max(1,1-\tau)$, $s_2=\min(N,N-\tau)$, and L is much greater than the possible AR filter orders (e.g. 50).

In step 916, two super matrices $T_X$ and $T_Y$ are formed as follows.

$$T_z = \begin{pmatrix} R_{3z}(-L) & R_{3z}(-L+1) & \cdots & R_{3z}(0) \\ R_{3z}(-L-1) & R_{3z}(-L) & \cdots & R_{3z}(-1) \\ \vdots & \vdots & \vdots & \vdots \\ R_{3z}(-2L) & R_{3z}(-2L+1) & \cdots & R_{3z}(-L) \end{pmatrix}$$

$z = X, Y$

From the assumption we made about the AR filter of the bispectral arrays, the orders $O_X$ and $O_Y$ of the AR filters of the bispectral arrays of $X_i(t)$ and $Y_i(t)$ are the ranks of the super matrices $T_X$ and $T_Y$. Therefore, $O_X$ and $O_Y$ are chosen by means of singular value decomposition. Having found the orders, the coefficients of the AR filters of the bispectral arrays are then obtained by solving the following linear system of equations:

$$\begin{pmatrix} R_{3z}(0) & R_{3z}(1) & \cdots & R_{3z}(O_z) \\ R_{3z}(-1) & R_{3z}(0) & \cdots & R_{3z}(O_z-1) \\ \vdots & \vdots & \vdots & \vdots \\ R_{3z}(-O_z) & R_{3z}(-O_z+1) & \cdots & R_{3z}(0) \end{pmatrix} \begin{pmatrix} 1 \\ b_{1z} \\ \vdots \\ b_{O_z z} \end{pmatrix} = \begin{pmatrix} \beta_z \\ 0 \\ \vdots \\ 0 \end{pmatrix}$$

$z = X, Y$ where the skewness ($\beta_z$) and the coefficients ($b_{1z}, \ldots, b_{O_z z}$), z=X, Y, can be obtained by solving the linear system of equations.

The average auto/cross complex triple product of $X_i(t)$ and $Y_i(t)$ are computed in step 918 as the cubic root of the triple product of the skewnesses, $(\beta_X \beta_Y \beta_Y)^{1/3}$, divided by the triple product of the Fourier transforms of the AR filter coefficients ($H_z(f)$), i.e., $$BC(f_1, f_2) = (\beta_X \beta_Y \beta_Y)^{1/3} / (H_X(f_1)H_Y(f_2)H_Y^*(f_1+f_2))$$

$$H_z(f) = 1 + \sum_{i=1}^{O_z} b_{iz}e^{-j2\pi fi}$$

$z = X, Y$ and $BR(f_1,f_2)$ is the average auto/cross real triple product:

$BR(f_1,f_2)=P_X(f_1)P_Y(f_2)P_Y(f_1+f_2)$

After obtaining the average auto/cross complex and real triple products, the system computes the bispectral density, biphase, and bicoherence arrays in step 920 the same way as in steps 816, 818, 820. In step 922, the system returns the requested bispectral arrays to the Data Computation Unit 30.

Development and Utilization of Diagnostic/Monitoring Indices

An index may be constructed using the bispectral arrays and/or other frequency and time domain features. Such an index may be designed to be predictive of the presence or absence of a given disease state. The index may be designed as a classifier, in which an individual to be assessed is predicted as having the disease or not, or in which the probability of having the disease is used as a measure of disease progression. The index may alternately be designed as a continuous predictor of neurological function or disease state/progression. Development of such indices requires a data set consisting of EEG data from individuals with the specified pathological condition, at different levels of progression, as well as control individuals without the specified condition. The data set must also include an independent assessment of the disease state that the index is designed to predict.

In the preferred embodiment, an index is constructed as a continuous predictor of disease state. EEGs are recorded from elderly normal controls and from patients with either mild to moderate Alzheimer's type dementia (ATD) or multi-infarct dementia (MID). EEG data is recorded when the subjects are in an awake, resting state. To fulfill the need for an independent assessment of disease progression, a Mini-Mental State Exam (MMSE; Folstein, 1975) is performed on each subject as a measure of dementia. The EEG autobispectral arrays are calculated for all frequency triples of the form ($f_1$, $f_2$, $f_1+f_2$) at 1 Hz resolution using 2-sec records of the first 30 seconds of non-drowsy, artifact-free EEG recorded from T3-Fp1 (International 10/20 Electrode Montage System). Statistical assessments are calculated using Spearman rank correlation and Mann-Whitney U non-parametric tests, as appropriate. A statistical significance level of P<0.05 is considered statistically significant.

The level of dementia as measured by mean MMSE score is statistically different between the control group and each dementia group, but not between dementia groups (Table 1).

TABLE 1

| Group | Number of Subjects | MMSE (mean ± SD) |
|---|---|---|
| Control | 18 | 29.0±1.1 |
| Alzheimer's Type Dementia | 11 | 16.6±8.6 |
| Multi-infarct Dementia | 7 | 19.4±7.5 |

Figure 4:
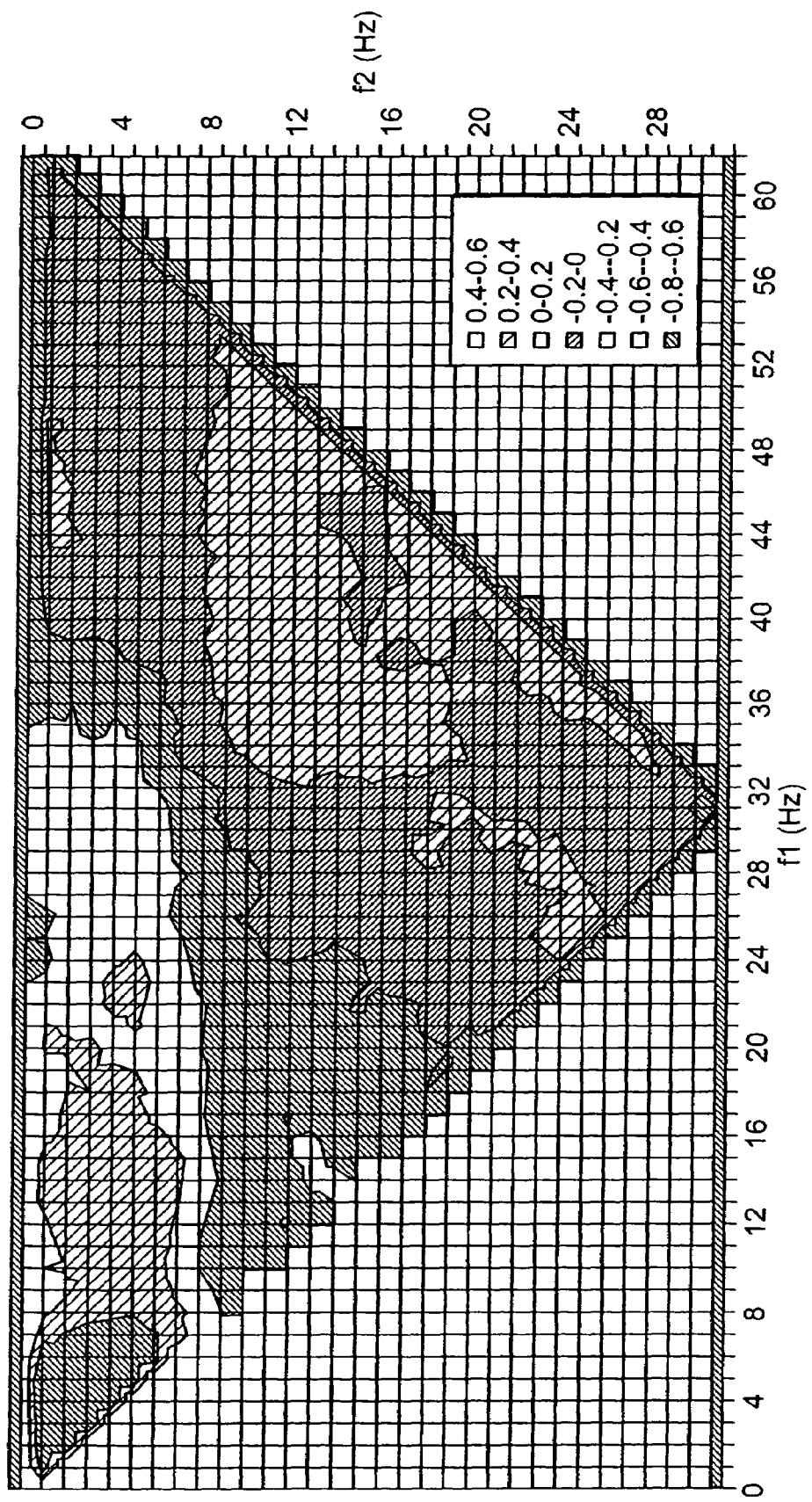
FIG. 4 is a graph of a Spearman correlation between EEG auto bispectral density and Mini Mental State Exam score.

The Spearman correlation between the values of individual frequency pairs ($f_1$,$f_2$) of the autobispectral density array and MMSE of all subjects is shown in FIG. 4. Recall that due to symmetry conditions, the bispectral density arrays are limited to $0 \leq f_2 \leq f_1$, and $f_1+f_2 \leq f_s/2$. Here, the upper frequency bound, $f_s/2$, is set to 64 Hz. The correlation with MMSE score is systematically negative for low frequencies [$f_1$<6 Hz, $f_2$<6 Hz], reaching a minimum of −0.659 at ($f_1$=3 Hz, $f_2$=2 Hz). Similarly, the correlation with MMSE score is systematically positive for high frequencies [$f_1$>34 Hz, $f_2$>10 Hz], reaching a maximum of 0.529 at ($f_1$=40 Hz, $f_2$=10 Hz).

A diagnostic or monitoring index is often specified to have the form of a linear predictor. Those skilled in the art will readily recognize that other forms, such as non-linear predictors, neural networks, measures derived from fractal spectral analysis and information theoretic metrics such as entropy and complexity may be used as well. In the preferred embodiment, the index has the general form $$\text{Index} = c_0 + \sum_{i=1}^{p} c_i F_i$$

where $c_0$ is a constant, {$F_i$, i=1, 2, . . . , p} are a set of features, {$c_i$, i=1, 2, . . . , p} are a set of coefficients corresponding to the features and p is the number of features. In the preferred embodiment, a set of features is constructed from the mean value of the regions within the EEG bispectral density array of a single EEG channel that exhibits a strong correlation with MMSE score, as noted above and in FIG. 4. Although the preferred embodiment uses one channel of EEG data, alternate embodiments may include data from a plurality of channels. The features derived from the bispectral density array that best correlated with MMSE score are the mean values of the regions [0 Hz≤$f_1$≤5 Hz, 9 Hz≤$f_2$≤$f_1$ Hz] and [35 Hz≤$f_1$≤53 Hz, 11 Hz≤$f_2$≤upper limit].

$$F_1 = \frac{1}{A_1} \sum_{i=0}^{5} \sum_{j=0}^{i} BD(f_1 = i, f_2 = j)$$

$$F_2 = \frac{1}{A_2} \sum_{i=35}^{53} \sum_{j=11}^{64-i} BD(f_1 = i, f_2 = j)$$

where $A_1$ and $A_2$ are the number of frequency pairs in the summation in the calculation of $F_1$ and $F_2$, respectively, and $0 \leq j \leq i$. The correlations of $F_1$ and $F_2$ with MMSE are −0.59 and 0.49, respectively.

Features may also be specified as ratios of values derived from the bispectral arrays. In the preferred embodiment, a third feature $F_3$ is specified as the ratio of $F_1$ to $F_2$.

$$F_3 = \frac{F_1}{F_2}$$

A simple index to track progression of dementia, as quantified by MMSE score, may be constructed as $$c_0 = \frac{-100 \min(F_3)}{(\max(F_3) - \min(F_3))}$$

$$c_3 = \frac{100}{(\max(F_3) - \min(F_3))}$$

$$\text{Index}_{\text{Dem\_progression}} = c_0 + c_3 F_3$$

Here, $c_3$ is defined such that the range of $\text{Index}_{Dem\_progression}$ will be between 0 and 100, inclusive by using the values min and max, the minima and maxima, respectively. Based upon the database used to derive this example, min($F_3$)=0.9, max ($F_3$)=2.6, resulting in $c_0$=−52.9 and $c_3$=58.8. The correlation of $F_3$ and thus of $\text{Index}_{Dem\_progression}$ with MMSE is −0.64, indicating that $\text{Index}_{Dem\_progression}$ is a sensitive measure of the degree of dementia.

Alternatively, an index may be derived to diagnose disease state. In an alternate embodiment, the described data set was used to derive an index capable of discriminating patients with diagnosed dementia from normal controls. The features derived from the bispectral density array that best discriminated controls from demented patients are the mean values of the regions [39 Hz≦$f_1$≦41 Hz, 9 Hz≦$f_2$≦11 Hz] and [2 Hz≦$f_1$≦4 Hz, 1 Hz≦$f_2$≦3 Hz].

$$F_4 = \frac{1}{A_4} \sum_{i=39}^{41} \sum_{j=9}^{11} BD(f_1 = i, f_2 = j)$$

$$F_5 = \frac{1}{A_5} \sum_{i=2}^{4} \sum_{j=1}^{3} BD(f_1 = i, f_2 = j)$$

$$F_6 = \frac{F_4}{F_5}$$

As before, $A_4$ and $A_5$ are the number of frequency pairs in the summation in the calculation of $F_4$ and $F_5$.

$$c_0 = \frac{-100\min(F_6)}{(\max(F_6) - \min(F_6))}$$

$$c_6 = \frac{100}{(\max(F_6) - \min(F_6))}$$

$$Index_{Control\_Dem} = c_0 + c_6 F_6$$

As before, $c_0$ and $c_6$ are defined such that the range of $Index_{Control\_Dem}$ will be between 0 and 100, inclusive. Based upon the database used to derive this example, $\min(F_6)$=0.4, $\max(F_6)$=1.1, resulting in $c_0$=−57.1 and $c_6$=142.9. Using a threshold value of 50, $Index_{Control\_Dem}$ differentiated patients diagnosed with dementia from normal control subjects with a sensitivity of 94%, a specificity of 83%, and area under the receiver operating curve (AUC) of 95%.

Similarly, the region that best separated ATD from MID patients was the mean value of the region [5 Hz≦$f_1$≦7 Hz, 5 Hz≦$f_2$≦7 Hz].

$$F_7 = \frac{1}{A_7} \sum_{i=5}^{7} \sum_{j=5}^{7} BD(f_1 = i, f_2 = j)$$

As before, $A_7$ is the number of frequency pairs in the summation in the calculation of $F_7$.

$$c_0 = \frac{-100\min(F_7)}{(\max(F_7) - \min(F_7))}$$

$$c_7 = \frac{100}{(\max(F_7) - \min(F_7))}$$

$$Index_{ATD\_MID} = c_0 + c_7 F_7$$

As before, $c_0$ and $C_7$ are defined such that the range of $Index_{ATD\_MID}$ will be between 0 and 100, inclusive. Based upon the database used to derive this example, $\min(F_7)$=0.5, $\max(F_7)$=6.5, resulting in $c_0$=−333.3 and $C_7$=66.7. Using a threshold value of 50, $Index_{ATD\_MID}$ differentiated ATD patients from MID patients with a sensitivity of 82%, a specificity of 86%, and an AUC of 91%.

In another alternate embodiment of the invention the system and method generate an index that predicts the efficacy of drug treatment or measures the state of a disease or condition. Such indices that assess the level of depression or use pre-treatment EEG data to predict the response of patients with depression to pharmacological treatment will now be described.

EEGs were recorded from 50 adults with major unipolar depression entered in a double-blind study evaluating the efficacy of antidepressant medications. Patients in the study were treated with either fluoxetine (n=12) or venlafaxine (n=13) versus placebo (n=25). Serial EEG recordings were made from awake, resting patients at pre-treatment (unmedicated) baseline, drug wash-in, and 48 hrs, 1, 2, 4, and 8 weeks after initial treatment. Hamilton Depression Rating Scale (Hamilton-D; Hamilton, 1960) was assessed at each recording period. Responders were defined as having Hamilton-D score ≦10 at week 8. The EEG bispectral density arrays were calculated for all frequency pairs ($f_1$, $f_2$) at 1 Hz resolution using 2-second records of the first 20–32 seconds of artifact-free EEG recorded from T3-Fp1 (International 10/20 Electrode Montage System). Statistical assessments were calculated using Spearman rank correlation and Mann-Whitney U non-parametric tests, as appropriate. A statistical significance level of P<0.05 was considered statistically significant.

Figure 5:
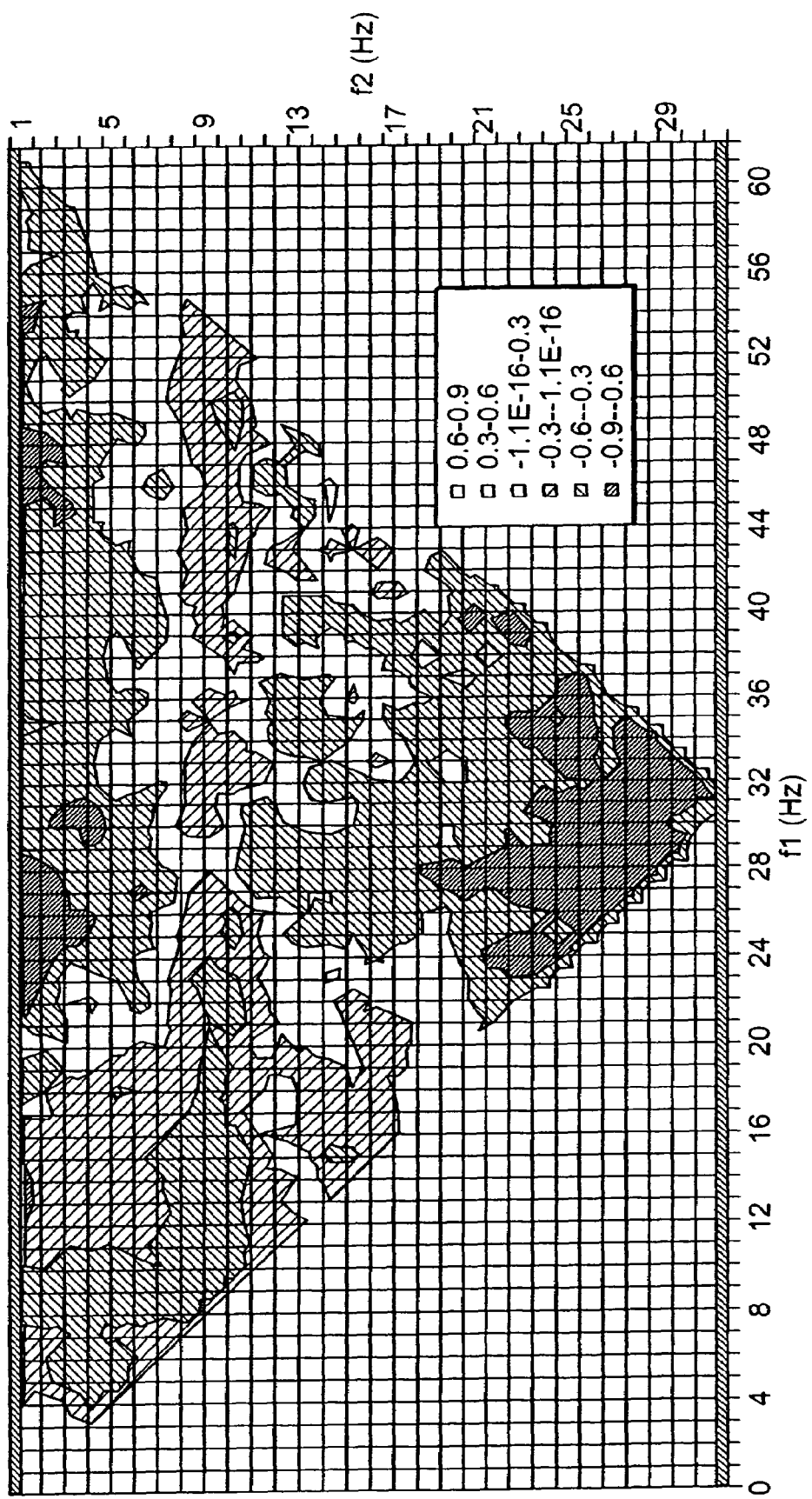
FIG. 5 is a graph of a Spearman correlation between EEG auto bispectral density and pre-medication baseline Hamilton Depression score.

The Spearman correlation between the values of individual frequency pairs ($f_1$, $f_2$) of the autobispectral density array and Hamilton-D scores at baseline of subjects receiving venlafaxine is shown in FIG. 5. Baseline depression, as quantified by Hamilton-D scores at baseline, was not significantly different between patients who responded to antidepressant treatment (responders) and those who did not (non-responders) (Table 2).

TABLE 2

| Group | Number of Subjects | Hamilton-D Score (mean ± SD) |
| --- | --- | --- |
| Responders | 18 | 21.9 ± 2.6 |
| Non-responders | 11 | 23.1 ± 4.2 |

The EEG bispectral density array was greater at all frequencies in more deeply depressed patients (i.e., lower Hamilton-D score), particularly in the region [12 Hz<$f_1$<24 Hz, 0<$f_2$<6 Hz]. An index to assess severity of depression may be derived from this data as $$F_{10} = \frac{1}{A_{10}} \sum_{i=13}^{23} \sum_{j=1}^{5} BD(f_1 = i, f_2 = j)$$

$$c_0 = \frac{-100\min(F_{10})}{(\max(F_{10}) - \min(F_{10}))}$$

$$c_{10} = \frac{100}{(\max(F_{10}) - \min(F_{10}))}$$

$$Index_{Depression\_Severity} = c_0 + c_{10} F_{10}$$

As before, $c_0$ and $c_{10}$ are defined such that the range of $Index_{Depression\_Severity}$ will be between 0 and 100, inclusive. Based upon the database used to derive this example, $\min(F_{10})$=3.9, $\max(F_{10})$=6.1, resulting in $c_0$=−177.3 and $c_{10}$=45.5. The correlation of $F_{10}$ and thus $Index_{Depression\_Severity}$ with Hamilton-D score is 0.31 (p<0.001). $Index_{Depression\_Severity}$ may be used as an objective method of assessing the level of depression, as a method of making a diagnosis or as a method of assessing the efficacy of treatment.

The EEG bispectral density measured at the pre-treatment baseline showed characteristic differences between responders and non-responders to medication, but not placebo. The largest differences were observed in the regions incorporated in features $F_{11}$ and $F_{12}$.

$$F_{11} = \frac{1}{A_{11}} \sum_{i=1}^{9} \sum_{j=1}^{i} BD(f_1 = i, f_2 = j)$$

$$F_{12} = \frac{1}{A_{12}} \sum_{j=25}^{32} \sum_{i=j}^{64-j} BD(f_1 = i, f_2 = j)$$

Patients who responded to venlafaxine had smaller $F_{11}$ values, a quantification of low frequency mean bispectral density in the range [0<$f_1$<10 Hz, 0<$f_2$<10 Hz]. Responders also had larger $F_{12}$ values, a quantification of high frequency mean bispectral density in the range [24 Hz<$f_1$<38 Hz, $f_2$>24 Hz]. A new feature ($F_{13}$) was defined as the ratio of the mean bispectral density in these two regions.

$$F_{13} = \frac{F_{12}}{F_{11}}$$

$$c_0 = \frac{-100 \min(F_{13})}{(\max(F_{13}) - \min(F_{13}))}$$

$$c_{13} = \frac{100}{(\max(F_{13}) - \min(F_{13}))}$$

$$\text{Index}_{Venlafaxine\_Response} = c_0 + c_{13} F_{13}$$

As before, $c_0$ and $c_{13}$ are defined such that the range of the venlafaxine response index ($\text{Index}_{Venlafaxine\_Response}$) will be between 0 and 100, inclusive. Based upon the database used to derive this example, min($F_{13}$)=0.4, max ($F_{13}$)=0.9, resulting in $c_0$=−80.0 and $c_{13}$=200.0. Using a threshold value of 50, $\text{Index}_{Venlafaxine\_Response}$ predicted responders with a sensitivity of 75%, a specificity of 77%, and an AUC of 81%. $\text{Index}_{Venlafaxine\_Response}$ may be used to predict the responsiveness of a specific patient to treatment with venlafaxine. Other indices may be derived from databases of patients treated with different antidepressant agents, such as fluoxetine. By using such a set of indices, a physician may determine which antidepressant agent is likely to have the greatest treatment response, thus simplifying the trial and error aspect of treating depression. Such a set of indices could also be used to predict the success of treatment with any particular set of antidepressant agents. These indices may be further refined by including in the development database different initial dosages of the various antidepressant agents. This will enable the index or indices to predict not only the most efficacious agent but also the most efficacious initial dose.

Although the invention has been described with respect to indices derived from the bispectral density array, it is not limited to such indices. Features may be calculated from other regions of the various bispectral arrays (i.e., complex triple product, real triple product, biphase and bicoherence, all for both auto and cross formulations). Other features may also be used to derive features, such as medians, standard deviations and variances, percentiles, absolute power within a region bounded by specified frequencies, relative power (absolute power as a percentage of total power within a region bounded by specified frequencies), neural networks, fractal spectral analysis, measures derived from information theory such as entropy and complexity, and other statistical measures known to those skilled in the art. Features may also be derived from the power spectrum and from various methods of time domain analysis such as pattern matching and fractal analysis. Features may also quantify the presence or absence of a specific condition over time period, or the degree to which a specific condition is met over a specific time period (e.g., the percent of time in a recent period that the power in a specific frequency band of a power or bispectral array was less than a threshold value). Detectors of specific conditions or signal types may also be used as features or as an index having just two states.

A further refinement of the system and method of the present invention is to incorporate features derived from the EEG with features derived from analysis of images of the structure under examination (e.g., the brain). Such images may be obtained from CAT (computer-aided tomography), MRI (magnetic resonance imaging), PET (positron emission tomography), X-ray and other modalities. Yet another refinement is to incorporate both features derived from the EEG with features derived from the analysis of images of the function of the structure under analysis. Images of function such as glucose metabolism may be obtained with techniques such as functional PET imaging. Features derived from metrics of the instantaneous or time-averaged glucose metabolism in the entire brain or a specified sub-region of the brain may be combined in an index of CNS function to quantify cognitive function, disease state, disease progression, and other parameters of interest.

Testing Methodologies to Improve Sensitivity and Specificity

The sensitivity and specificity of the invention may be increased through the use of differential testing methodologies. Differential test methodologies use 2 or more consecutive assessments, and analyze the change in the value of the test metric as well as the actual values at each of the assessments. The assessments are generally conducted under different conditions, such as sleep or under the influence of a stressor such as a mental task; these are compared to a baseline assessment. Patients with dementia, depression and other neurological disorders exhibit EEG responses different from that of normal subjects in a differential testing methodology. Several differential testing methodologies may be used to increase the performance of the derived indices. Preferably, the test metric is an index derived from the EEG bispectral arrays, as well as other non-bispectral parameters, and will be denoted in the description below as INDEX.

The first test methodology uses the difference between a first value of INDEX calculated from EEG acquired with the subject's eyes open and a second value of INDEX calculated from EEG acquired with the subject's eyes closed. The electrodes 15 are first applied to the subject 10, who is instructed to sit quietly with eyes open. A segment of EEG is acquired by the DAU 20 and transmitted to the DCU 30 for analysis. Generally, segments of several minutes are used to calculate the INDEX values. The subject 10 is next directed to sit quietly with eyes closed, and a second segment of EEG is acquired by the DAU 20 and transmitted to the DCU 30 for analysis. The DCU calculates INDEX values for both the first and second periods of acquired data, referred to as $\text{INDEX}_{eyes\_open}$ and $\text{INDEX}_{eyes\_closed}$. Examining the acquired data for artifact and either removing the detected artifact or excluding the artifacted portion of the acquired data from analysis is an integral part of calculating an INDEX value. The numerical difference between $INDEX_{eyes\_open}$ and $INDEX_{eyes\_closed}$ is a metric that is indicative of the level of neurological dysfunction, the severity of a condition or a prediction of the efficacy of treatment.

A second test methodology uses the difference between a first value of INDEX calculated from EEG acquired with the subject in a relaxed state and a second value of INDEX calculated from EEG acquired while the subject is performing a mental calculation task. The subjects may be directed to keep their eyes open during both recording periods. Alternatively, the subjects may be directed to close their eyes during both recording periods, though this may restrict the mental calculation tasks that may be chosen. The mental calculation task may be any simple task or set of tasks chosen to provide adequate difficulty yet universal enough to not require special training or a level of education not universal in the population to be tested. Two example tasks are mental addition and subtraction of numbers, as would be required in balancing a check book, and the calculation of the number of days between two dates. The electrodes are first applied to the subject, who is instructed to sit quietly with eyes open. A segment of EEG is acquired by the DAU 20 and transmitted to the DCU 30 for analysis. Again, segments of several minutes are used to calculate the INDEX values. The subject is next given instruction in the mental task and then asked to complete it. A second segment of EEG is acquired by the DAU 20 during the period of mental calculation. The acquired data is then transmitted to the DCU 30 for analysis. The DCU 30 calculates INDEX values for both the first and second periods of acquired data, referred to as $INDEX_{baseline}$ and $INDEX_{task}$. The numerical difference between $INDEX_{baseline}$ and $INDEX_{task}$ is a second metric that is indicative of the level of neurological dysfunction, the severity of a condition or a prediction of the efficacy of treatment.

It has been reported that EEG methods of differentiating subjects with ATD from normal controls exhibit higher sensitivity and specificity during REM sleep than during wakefulness. Therefore, a third test methodology uses the difference between a first value of INDEX calculated from EEG acquired with the subject in an awake, relaxed state and a second value of INDEX calculated from EEG acquired while the subject is sleeping. The electrodes 15 are first applied to the subject 10, who is instructed to sit quietly with eyes either open or closed. A segment of EEG is acquired by the DAU 20 and transmitted to the DCU 30 for analysis. Again, segments of several minutes are used to calculate the INDEX values. The subject then goes to sleep and EEG data is acquired continuously while the subject is sleeping. The second INDEX value is calculated from EEG recorded while the subject is sleeping, preferably in REM sleep. For this reason, it is preferable that the DCU software implements any of the algorithms known in the art that perform automated identification of REM sleep. These algorithms generally make use of EEG data as well as electrooculograph (EOG) data. Alternately, a trained observer who visually reviews the recorded EEG and enters the starting and ending times of REM sleep into the DAU 20 may identify periods of REM sleep manually. In this case, it is necessary that the DAU 20 have a data entry device such as a computer keyboard. The acquired data is then transmitted to the DCU 30 for analysis. The DCU 30 calculates an INDEX value for the first period of acquired data, which is referred to as $INDEX_{awake}$. The DCU 30 next calculates an INDEX value from the second period of acquired data, referred to as $INDEX_{sleep}$. Because $INDEX_{sleep}$ is preferably calculated during a period of REM sleep, the automatic REM sleep identification algorithm must first process the data in order to identify a suitable segment of REM sleep from which to calculate $INDEX_{sleep}$. If the recorded EEG data is manually reviewed for periods of REM sleep, the starting and ending times transmitted to the DCU 30 are used instead. The numerical difference between $INDEX_{awake}$ and $INDEX_{sleep}$ is a metric that is indicative of the level of neurological dysfunction, the severity of a condition or a prediction of the efficacy of treatment. This type of processing extends to any observation of INDEX changes between or during the awake and asleep states, not simply the comparison with baseline.

Figure 6:
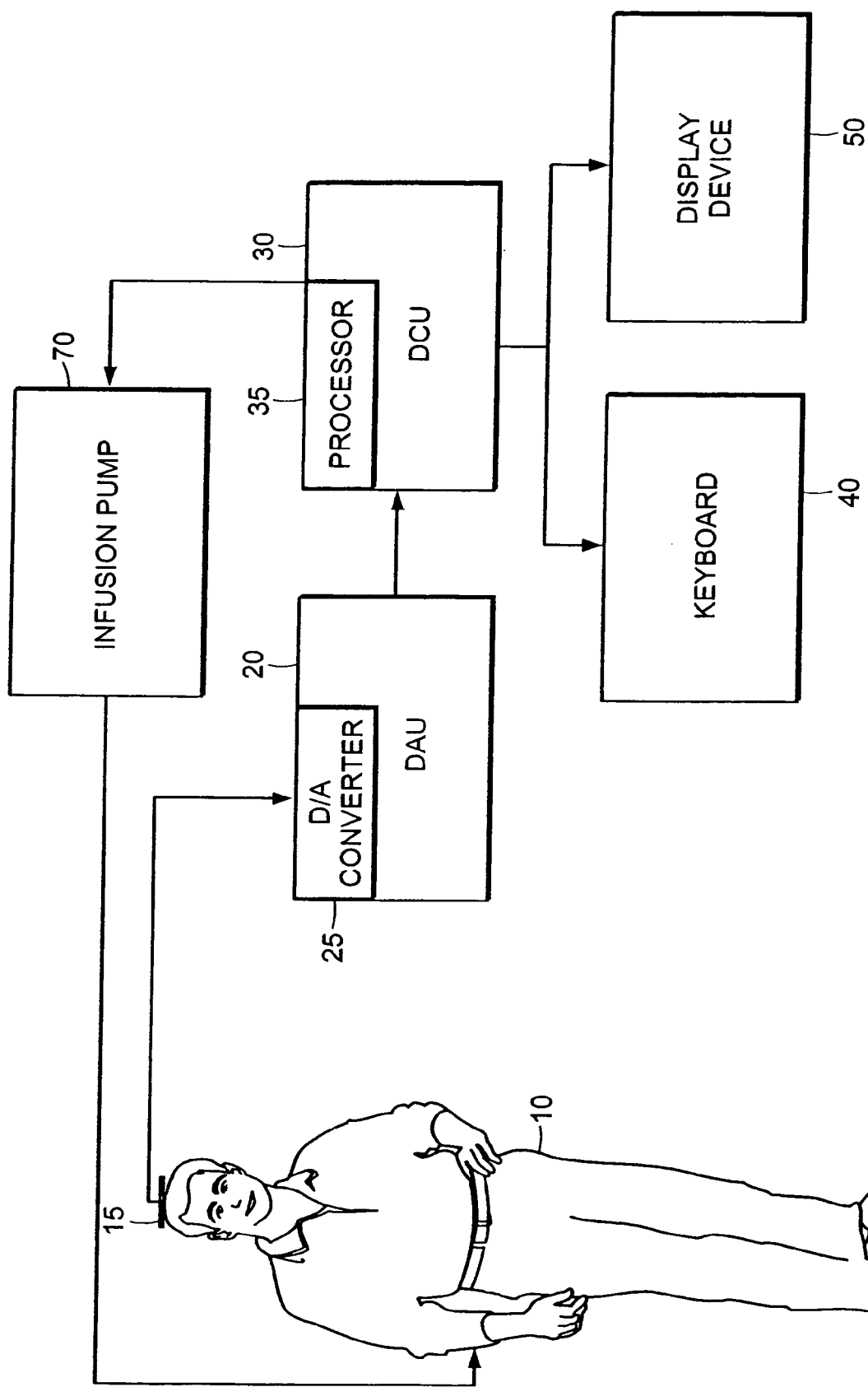
FIG. 6 is a block diagram of an alternate embodiment of the system of the present invention, incorporating an infusion pump.

A further embodiment of the invention utilizes the difference between the value of an INDEX computed from a subject's resting, awake EEG and the value of the INDEX computed from EEG obtained after administration of a hypnotic anesthetic agent. Preferably, the anesthetic agent is administered manually by means of a syringe. Alternatively, a means of administering such an anesthetic agent is incorporated into the system as shown in FIG. 6, generally a computer-controlled infusion pump 70, or in the case of an inhalational agent, an anesthesia machine designed for administering volatile agents. The infusion pump may be a commercially available type such as a Graseby Model 3400/3500. The infusion pump is controlled by the DAU 20 via a standard RS-232 communication link.

The EEG electrodes are first applied to the subject 10. If an infusion pump 70 is used, an intravenous line is placed in the subject's forearm by the clinician who is administering the examination, the pump is loaded with a syringe of the chosen hypnotic anesthetic agent and the intravenous line is connected to the infusion pump. Preferably, the subject is directed to keep his/her eyes open during both recording periods. Alternately, the subject may be directed to close his/her eyes during both recording periods. A segment of EEG is acquired by the DAU 20 and transmitted to the DCU 30 for analysis. Segments of several minutes are used to calculate the INDEX values. Upon completion of the baseline recording period, the clinician administers a bolus of hypnotic agent, preferably 0.5 mg/kg of thiopental. If an infusion pump is in use, the DAU 20 instructs the infusion pump to deliver the bolus of anesthetic agent. A second segment of EEG is acquired by the DAU 20 after the bolus of anesthetic agent has reached its maximal effect, generally 3–5 minutes in the preferred embodiment. The acquired data is then transmitted to the DCU 30 for analysis. The DCU 30 calculates INDEX values for both the first and second periods of acquired data, referred to as $INDEX_{baseline}$ and $INDEX_{agent}$. The numerical difference between the pre-medication baseline value $INDEX_{baseline}$ and the post-medication value $INDEX_{agent}$ is a metric that is indicative of the level of neurological dysfunction, the severity of a condition or a prediction of the efficacy of treatment. For example, subjects with ATD exhibited smaller differences in absolute beta power than non-demented control subjects between baseline and post thiopental administration.

The DAU 20 may be equipped with display and data entry devices, such as a computer monitor and keyboard, respectively. The DAU 20 will execute an interface program that will allow communication between the infusion pump and the DAU 20. The DAU 20 may also calculate the volume of infusate, requiring the clinician to enter only the subject's weight and the dilution of the anesthetic agent. If the infusion pump is in use, the clinician may also control the rate of infusion of the anesthetic agent via the interface program. Conversely, the infusion pump may provide information to the DAU 20, confirming its operational status and the administration of the desired bolus of anesthetic agent.

In another alternate embodiment, the anesthetic agent may be increased in a step-wise regimen consisting of at least two steps, or it may be increased continuously. This is most easily implemented using the infusion pump and interface program previously described and may be preprogrammed into the interface program. This embodiment makes use of a pharmacokinetic (PK) model, which provides a calculated blood plasma concentration from a time series of discrete doses of an anesthetic. The PK model may be integrated with the interface software of the infusion pump, the calculated time series of anesthetic agent doses being communicated to the pump interface software and being used by that software to determine the pump infusion rate. PK software is readily available from several public domain sources; the preferred embodiment uses the RUG-LOOP software freely available from Michel Struys, M.D., Department of Anaesthesia, University of Gent, De Pintelaan 185, B-9000 Gent, Belgium. Alternatively, the PK software STANPUMP may be used (freely available from the author, Steven L. Shafer, M.D., Anesthesiology Service (112A), PAVAMC, 3801 Miranda Ave, Palo Alto, Calif. 94304).

While the foregoing invention has been described with reference to its preferred embodiments, various alterations and modifications will occur to those skilled in the art. All such alterations and modifications are intended to fall within the scope of the appended claims.

What is claimed is:

1. A system of assessing neurological conditions comprising:
   one or more electrodes for acquiring biopotential signals,
   a processor for deriving, from said biopotential signals, Kth-order spectral values, where K is an integer greater than 1, and deriving from said Kth order spectral values features indicative of neurological conditions, said processor using a differential testing methodology to derive said features.

2. The system of claim 1 further comprising an infusion device connected to said processor for administering a controlled dose of a pharmacological agent as part of said differential testing methodology.

3. A method of assessing neurological conditions comprising the steps of
   acquiring biopotential signals,
   deriving, from said biopotential signals, Kth-order spectral values, where K is an integer greater than 1, and
   deriving at least one feature indicative of neurological conditions from said Kth order spectral using a differential test methodology.

4. The method of claim 3 further comprising the step of administering a controlled dose of a pharmacological agent as part of said differential test methodology.

5. A method of assessing neurological conditions comprising the steps of:
   acquiring biopotential signals from a human subject,
   deriving, from said biopotential signals, Kth-order spectral values, where K is an integer greater than 1, and
   deriving from said Kth order spectral values a prediction of the effectiveness of a specific therapeutic intervention at least one hour after said intervention.

6. A system of assessing neurological conditions comprising
   one or more electrodes for acquiring biopotential signals and
   a processor for deriving, from said biopotential signals, Kth-order spectral values, where K is an integer greater than 1 and for deriving from said Kth order spectral values a prediction of the effectiveness of a specific therapeutic intervention at least one hour after said intervention.

7. A system of assessing neurological conditions comprising:
   one or more electrodes for acquiring biopotential signals, and
   a processor for deriving, from said biopotential signals, at least one feature indicative of neurological conditions, one of said at least one feature being a prediction of the effectiveness of a therapeutic intervention in achieving a desired behavioral effect at least one hour after said intervention,
   wherein said at least one feature indicative of neurological conditions is a $K^{th}$-order spectral value, where K is an integer greater than 1.

8. A system of assessing neurological conditions comprising:
   one or more electrodes for acquiring biopotential signals, and
   a processor for deriving, from said biopotential signals, at least one feature indicative of neurological conditions, one of said at least one feature being a prediction of the effectiveness of a therapeutic intervention in achieving a desired behavioral effect at least one hour after said intervention,
   wherein said at least one feature indicative of neurological conditions is a statistical measure.

9. A system of assessing neurological conditions comprising:
   one or more electrodes for acquiring biopotential signals, and
   a processor for deriving, from said biopotential signals, at least one feature indicative of neurological conditions, one of said at least one feature being a prediction of the effectiveness of a therapeutic intervention in achieving a desired behavioral effect at least one hour after said intervention,
   wherein said at least one feature indicative of neurological conditions is a time domain measure.

10. A system of assessing neurological conditions comprising:
    one or more electrodes for acquiring biopotential signals, and
    a processor for deriving, from said biopotential signals, at least one feature indicative of neurological conditions, one of said at least one feature being a prediction of the effectiveness of a therapeutic intervention in achieving a desired behavioral effect at least one hour after said intervention,
    wherein said at least one feature indicative of neurological conditions is a cordance measure.

11. A system of assessing neurological conditions comprising:
    one or more electrodes for acquiring biopotential signals, and
    a processor for deriving, from said biopotential signals, at least one feature indicative of neurological conditions, one of said at least one feature being a prediction of the effectiveness of a therapeutic intervention in achieving a desired behavioral effect, said processor using a differential testing methodology to derive said at least one feature.

12. The system of claim 11 further comprising an infusion device connected to said processor for administering a controlled dose of a pharmacological agent as part of said differential testing methodology.

13. A method of assessing neurological conditions comprising the steps of:
acquiring biopotential signals from a human subject, and
deriving from said biopotential signals at least one feature indicative of neurological conditions, one of said at least one feature being a prediction of the effectiveness of a therapeutic intervention in achieving a desired behavioral effect at least one hour after said intervention,
wherein said feature indicative of neurological conditions $K^{th}$-order spectral value, where K is an integer greater than 1.

14. A method of assessing neurological conditions comprising the steps of:
acquiring biopotential signals from a human subject, and
deriving from said biopotential signals at least one feature indicative of neurological conditions, one of said at least one feature being a prediction of the effectiveness of a therapeutic intervention in achieving a desired behavioral effect at least one hour after said intervention,
wherein said feature indicative of neurological conditions is a statistical measure.

15. A method of assessing neurological conditions comprising the steps of:
acquiring biopotential signals from a human subject, and
deriving from said biopotential signals at least one feature indicative of neurological conditions, one of said at least one feature being a prediction of the effectiveness of a therapeutic intervention in achieving a desired behavioral effect at least one hour after said intervention,
wherein said feature indicative of neurological conditions is a time domain measure.

16. A method of assessing neurological conditions comprising the steps of:
acquiring biopotential signals from a human subject, and
deriving from said biopotential signals at least one feature indicative of neurological conditions, one of said at least one feature being a prediction of the effectiveness of a therapeutic intervention in achieving a desired behavioral effect at least one hour after said intervention,
wherein said feature indicative of neurological conditions is a cordance measure.

17. A method of assessing neurological conditions comprising the steps of
acquiring biopotential signals, and
deriving, from said biopotential signals, at least one feature indicative of neurological conditions, said features being derived using a differential testing methodology, wherein said at least one feature indicative of neurological conditions is a prediction of the effectiveness of a therapeutic intervention in achieving a desired behavioral effect.

18. The method of claim 17, wherein said prediction is derived before an initiation of said therapeutic intervention.

19. The method of claim 17, wherein said prediction is derived before the clinical appearance of said therapeutic intervention.

20. The method of claim 17 wherein a controlled dose of a pharmacological agent is administered as part of said differential testing methodology.

21. A method of assessing neurological conditions comprising the steps of:
acquiring biopotential signals from a human subject, and
deriving, from said biopotential signals, at least two features indicative of neurological conditions and,
combining said features into an index indicative of neurological conditions, said index being a prediction of the effectiveness of a therapeutic intervention in achieving a desired behavioral effect at least one hour after said intervention,
wherein said at least one feature indicative of neurological conditions is a Kth-order spectral value, where K is an integer greater than 1.

* * * * *

US007231245C1

(12) EX PARTE REEXAMINATION CERTIFICATE (8020th)

United States Patent
Greenwald et al.

(10) Number: US 7,231,245 C1
(45) Certificate Issued: Feb. 8, 2011

(54) SYSTEM AND METHOD OF ASSESSMENT OF NEUROLOGICAL CONDITIONS USING EEG

(75) Inventors: Scott D. Greenwald, Norfolk, MA (US); Charles P. Smith, Medway, MA (US); Jeffrey C. Sigl, Medway, MA (US); Phillip H. Devlin, Brookline, MA (US)

(73) Assignee: Aspect Medical Systems, Inc., Newton, MA (US)

Reexamination Request:
No. 90/010,657, Oct. 19, 2009

Reexamination Certificate for:
Patent No.: 7,231,245
Issued: Jun. 12, 2007
Appl. No.: 10/337,088
Filed: Jan. 6, 2003

Related U.S. Application Data

(60) Provisional application No. 60/345,433, filed on Jan. 4, 2002.

(51) Int. Cl.
*A61B 5/04* (2006.01)

(52) U.S. Cl. .................................................... 600/544
(58) Field of Classification Search ................... None
See application file for complete search history.

(56) References Cited

U.S. PATENT DOCUMENTS

| | | | |
|---|---|---|---|
| 4,407,299 A | 10/1983 | Culver | |
| 4,736,751 A | 4/1988 | Gevins et al. | |
| 4,862,359 A | 8/1989 | Trivedi et al. | |
| 5,083,571 A | 1/1992 | Prichep | |
| 5,119,816 A | 6/1992 | Gevins | |
| 5,299,569 A | 4/1994 | Wernicke et al. | |
| 5,331,970 A | 7/1994 | Gevins et al. | |
| 5,568,816 A | 10/1996 | Gevins et al. | |
| 5,743,860 A * | 4/1998 | Hively et al. | 600/544 |
| 5,871,517 A | 2/1999 | Abrams et al. | |
| 6,021,346 A * | 2/2000 | Ryu et al. | 600/544 |
| 6,066,163 A | 5/2000 | John | |
| 6,205,359 B1 | 3/2001 | Boveja | |
| 6,263,237 B1 | 7/2001 | Rise | |
| 6,304,775 B1 | 10/2001 | Iasemidis et al. | |
| 6,425,852 B1 | 7/2002 | Epstein et al. | |
| 6,459,936 B2 | 10/2002 | Fischell et al. | |
| 6,463,328 B1 | 10/2002 | John | |
| 6,539,263 B1 | 3/2003 | Schiff et al. | |
| 6,804,661 B2 * | 10/2004 | Cook | 706/20 |
| 7,206,632 B2 | 4/2007 | King | |
| 2002/0013612 A1 | 1/2002 | Whitehurst | |
| 2002/0013812 A1 | 1/2002 | Krueger et al. | |
| 2003/0023282 A1 | 1/2003 | Barrett et al. | |
| 2003/0135128 A1 | 7/2003 | Suffin et al. | |
| 2003/0181821 A1 | 9/2003 | Greenwald et al. | |
| 2003/0204135 A1 | 10/2003 | Bystritsky | |
| 2005/0043774 A1 | 2/2005 | Devlin et al. | |
| 2005/0216071 A1 | 9/2005 | Devlin et al. | |

FOREIGN PATENT DOCUMENTS

WO  WO-03057029 A2  7/2003
WO  WO-2004100765 A2  11/2004

OTHER PUBLICATIONS

Mayo Clinic, Antidepressant, Monoamine Oxidase (Mao) Inhibitor (Oral Route) at http://www.mayoclinic.com/health/drug-information/DR602071/DSECTION=proper%2Duse.last updated Nov. 1, 2009, viewed on Feb. 25, 2010.*

(Continued)

*Primary Examiner*—Jeanne M Clark

(57) ABSTRACT

The present invention is a system and method that produces features and indices that indicate the presence or absence of a disease or condition, or of the progression of a disease or condition. The system and method of the present invention also produce features and indices that predict responsiveness to medication from a premedication baseline. The system and method of the present invention further incorporates a testing methodology to improve the performance characteristics of the features or indices. To obtain such features and indices, time domain, power spectrum, bispectrum and higher order spectrum values are derived from biopotential signals taken from the subject being tested.

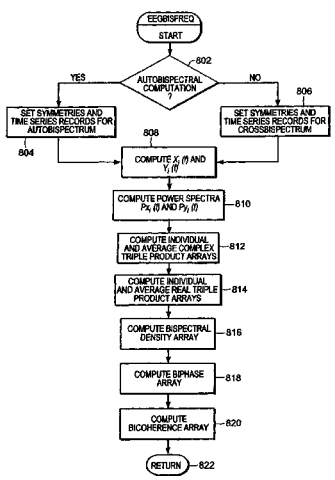

OTHER PUBLICATIONS

Leuchter et al., "Brain Structure and Function and the Outcomes of Treatment for Depression," Journal of Clinical Psychiatry 58 Suppl 16:22–31 (1997).*

Chabot et al., "Behavioral and Electrophysiologic Predictors of Treatment Response to Stimulants in Children with Attention Disorders," Journal Of Child Neurology 14(6):343–351 (1999).*

Suffin et al., U.S. Appl. No. 60/304,627.*

Luthringer et al., "All–night EER spectral analysis as a tool for the prediction of clinical response to antidepressant treatment," Biol Psychiatry 38:98–104 (1995).*

Sigl et al., "An introduction to bispectral analysis for the electroencephalogram," J Clinical Monitoring 10:392–404 (1994).*

Gangadahar et al., "Post–seizure EEG fractal dimension of first ECT predicts antidepressant response at two weeks," Journal of Affective Disorders 52:235–238 (1999).*

Jasper, H. H., "The Ten–Twenty Electrode System of the International Federation in Electroencephalography and Clinical Neurology," The EEG Journal, 10 (Appendix):371–75 (1958).

Murphy et al., Stimulation of the Nervous System for the Management of Seizures: CNS Drugs. 17(2):101–15 (2003).

Marqui et al., International Journal of Psychophysiology, 18:49–65 (1994).

Pizzagalli. et al., "Anterior Cingulate Activity as a Predictor of Degree of Treatment Response in Major Depression: Evidence from Brain Electrical Tomography Analysis", American Journal of Psychiatry, 158:3, 405–15 (2001).

Brent et al., "Early–Onset Mood Disorder", www.acnp.org/g4/GN40100158/CH154.html, printed Nov. 10, 2008.

Graae et al., "Abnormality of EEG Alpha Asymmetry in Female Adolescent Suicide Attempters", Biol. Phvschiatrv 40:706–13 (1996).

Hunter, et al. "Neurophysiologic Correlates of Side Effects in Normal Subjects Randomized to Venlafaxine or Placebo", Neurophysopharmacology 1–8 (2004).

Struve, F. A., "Electroencephalographic Relationship to Suicidal Behavior: Qualitative Considerations and a Report On a Series of Completed Suicides", Clin. Electroencephalography, vol. 14 (1): 20–26 (1983).

Struve, F. A., "Possible Potentiation of Suicide Risk in Patients with EEG Dysrhythmias Taking Oral Contraceptives: A Speculative Empirical Note", Clin. Electroencephalography, 16(2): 88–90 (1985).

Struve, F. A., Suicide and Life–Threatening Behavior, vol. 16(2), Ch. 3 "Clinical Electroencephalographv and a Study of Suicide Behavior", pp. 51–83 (Summer 1986).

* cited by examiner

US 7,231,245 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 8-11 and 14-17 are determined to be patentable as amended.

Claims 18 and 19, dependent on an amended claim, are determined to be patentable.

New claims 22-57 are added and determined to be patentable.

Claims 1-7, 12, 13, 20 and 21 were not reexamined.

8. A system of assessing neurological conditions comprising:
one or more electrodes for acquiring biopotential signals, and
a processor for deriving, from said biopotential signals, at least one feature indicative of neurological conditions, [one of] *and for generating, from* said at least one feature, *an index, said index* being a [prediction] *continuous predictor* of the effectiveness of a therapeutic intervention in achieving a desired behavioral effect at least one hour after said intervention,
wherein said at least one feature indicative of neurological conditions is a statistical measure.

9. A system of assessing neurological conditions comprising:
one or more electrodes for acquiring biopotential signals, and
a processor for deriving, from said biopotential signals, at least one feature indicative of neurological conditions, [one of] *and for generating, from* said at least one feature, *an index, said index* being a [prediction] *continuous predictor* of the effectiveness of a therapeutic intervention in achieving a desired behavioral effect at least one hour after said intervention,
wherein said at least one feature indicative of neurological conditions is a time domain measure.

10. A system of assessing neurological conditions comprising:
one or more electrodes for acquiring biopotential signals, and
a processor for deriving, from said biopotential signals, at least one feature indicative of neurological conditions, [one of] *and for generating, from* said at least one feature, *an index, said index* being a [prediction] *continuous predictor* of the effectiveness of a therapeutic intervention in achieving a desired behavioral effect at least one hour after said intervention,
wherein said at least one feature indicative of neurological conditions is a cordance measure.

11. A system of assessing neurological conditions comprising:
one or more electrodes for acquiring biopotential signals, and
a processor for deriving, from said biopotential signals, at least one feature indicative of neurological conditions, one of said at least one feature being a prediction of the effectiveness of a therapeutic intervention in achieving a desired behavioral effect, said processor using a differential testing methodology to derive said at least one feature, *wherein said differential testing methodology comprises at least two assessments conducted under different conditions.*

14. A method of assessing neurological conditions comprising the steps of:
acquiring biopotential signals from a human subject, and
deriving from said biopotential signals at least one feature indicative of neurological conditions, [one of] *and for generating, from* said at least one feature, *an index, said index* being a [prediction] *continuous predictor* of the effectiveness of a therapeutic intervention in achieving a desired behavioral effect at least one hour after said intervention
wherein said feature indicative of neurological conditions is a statistical measure.

15. A method of assessing neurological conditions comprising the steps of:
acquiring biopotential signals from a human subject, and
deriving from said biopotential signals at least one feature indicative of neurological conditions, [one of] *and for generating, from* said at least one feature, *an index, said index* being a [prediction] *continuous predictor* of the effectiveness of a therapeutic intervention in achieving a desired behavioral effect at least one hour after said intervention,
wherein said feature indictive of neurological conditions is a time domain measure.

16. A method of assessing neurological conditions comprising the steps of:
acquiring biopotential signals from a human subject, and
deriving from said biopotential signals at least one feature indicative of neurological conditions, [one of] *and for generating, from* said at least one feature, *an index, said index* being a [prediction] *continuous predictor* of the effectiveness of a therapeutic intervention in achieving a desired behavioral effect at least one hour after said intervention,
wherein said feature indicative of neurological conditions is a cordance measure.

17. A method of assessing neurological conditions comprising the steps of
acquiring biopotential signals, and
deriving, from said biopotential signals, at least one feature indicative of neurological conditions, said features being derived using a differential testing methodology, wherein said at least one feature indicative of neurological conditions is a prediction of the effectiveness of a therapeutic intervention in achieving a desired behavioral effect, *wherein said differential testing methodology comprises at least two assessments conducted under different conditions.*

*22. The system of claim 8 wherein said index ranges from a predetermined minimum value to a predetermined maximum value.*

*23. The system of claim 8 wherein said at least one feature comprises a bispectral feature.*

*24. The system of claim 8, wherein said at least one feature indicative of neurological conditions is derived from a single one of the biopotential signals.*

*25. The system of claim 8 wherein said processor uses a differential testing methodology to derive said at least one*

*feature, wherein said differential testing methodology comprises at least two assessments conducted under different conditions.*

*26. The system of claim 9 wherein said index ranges from a predetermined minimum value to a predetermined maximum value.*

*27. The sytem of claim 9 wherein said at least one feature comprises a bispectral feature.*

*28. The system of claim 9 wherein said processor generates said index from at least two features indicative of neurological conditions, wherein said at least two features comprise bispectral and non-bispectral features.*

*29. The system of claim 9 wherein said processor uses a differential testing methodology to derive said at least one feature, wherein said differential testing methodology comprises at least two assessments conducted under different conditions.*

*30. The system of claim 10 wherein said index ranges from a predetermined minimum value to a predetermined maximum value.*

*31. The system of claim 10 wherein said at least one feature comprises a bispectral feature.*

*32. The system of claim 10 wherein said processor generates said index from at least two features indicative of neurological conditions, wherein said at least two features comprise bispectral and non-bispectral features.*

*33. The system of claim 10 wherein said processor uses a differential testing methodology to derive said at least one feature, wherein said differential testing methodology comprises at least two assessments conducted under different conditions.*

*34. The system of claim 11 wherein said prediction is derived before an initiation of said therapeutic intervention.*

*35. The system of claim 11 wherein said prediction is derived before the clinical appearance of said therapeutic intervention.*

*36. The system of claim 11 wherein said differential testing methodology comprises at least two assessments both performed before an initiation of said therapeutic intervention.*

*37. The system of claim 11 wherein using said differential testing methodology to derive said at least one feature comprises analyzing a change in a value between at least two assessments.*

*38. The system of claim 11 wherein said at least one feature indicative of neurological conditions is a bispectral value.*

*39. The method of claim 14 wherein said index ranges from a predetermined minimum value to a predetermined maximum value.*

*40. The method of claim 14 wherein said at least one feature comprises a bispectral feature.*

*41. The method of claim 14, wherein said at least one feature indicative of neurological conditions is derived from a single one of the biopotential signals.*

*42. The method of claim 14 further comprising using a differential testing methodology to derive said at least one feature, wherein said differential testing methodology comprises at least two assessments conducted under different conditions.*

*43. The method of claim 15 wherein said index ranges from a predetermined minimum value to a predetermined maximum value.*

*44. The method of claim 15 wherein said at least one feature comprises a bispectral feature.*

*45. The method of claim 15 further comprising generating said index from at least two features indicative of neurological conditions, wherein said at least two features comprise bispectral and non-bispectral features.*

*46. The method of claim 15 further comprising using a differential testing methodology to derive said at least one feature, wherein said differential testing methodology comprises at least two assessments conducted under different conditions.*

*47. The method of claim 16 wherein said index ranges from a predetermined minimum value to a predetermined maximum value.*

*48. The method of claim 16 wherein said at least one feature comprises a bispectral feature.*

*49. The method of claim 16 further comprising generating said index from at least two features indicative of neurological conditions, wherein said at least two features comprise bispectral and non-bispectral features.*

*50. The method of claim 16 further comprising using a differential testing methodology to derive said at least one feature, wherein said differential testing methodology comprises at least two assessments conducted under different conditions.*

*51. The method of claim 17 wherein said differential testing methodology comprises at least two assessments both performed before an initiation of said therapeutic intervention.*

*52. The method of claim 17 wherein using said differential testing methodology to derive said at least one feature comprises analyzing a change in a value between at least two assessments.*

*53. The method of claim 17 wherein said at least one feature indicative of neurological conditions is a bispectral value.*

*54. A system of assessing neurological conditions comprising:*

*one or more electrodes for acquiring biopotential signals, and*

*a processor for deriving, from said biopotential signals, at least one feature indicative of neurological conditions, one of said at least one feature being a prediction of the effectiveness of a therapeutic intervention in achieving a desired behavioral effect at least one hour after said intervention,*

*wherein said at least one feature indicative of neurological conditions is a statistical measure, and*

*wherein said at least one feature indicative of neurological conditions is a bispectral value.*

*55. The system of claim 54 wherein said processor uses a differential testing methodology to derive said at least one feature.*

*56. A method of assessing neurological conditions comprising the steps of:*

*acquiring biopotential signals from a human subject, and*

*deriving from said biopotential signals at least one feature indicative of neurological conditions, one of said at least one feature being a prediction of the effectiveness of a therapeutic intervention in achieving a desired behavioral effect at least one hour after said intervention,*

*wherein said feature indicative of neurological conditions is a statistical measure, and*

*wherein said at least one feature indicative of neurological conditions is a bispectral value.*

*57. The method of claim 56 further comprising using a differential testing methodology to derive said at least one feature.*

\* \* \* \* \*